(12) United States Patent
Ptchelintsev et al.

(10) Patent No.: US 8,207,171 B2
(45) Date of Patent: *Jun. 26, 2012

(54) COSMETIC USE OF 1-AROYL-N-(2-OXO-3-PIPERIDINYL)-2-PIPERAZINE CARBOXAMIDES AND RELATED COMPOUNDS

(75) Inventors: Dmitri S. Ptchelintsev, Jersey City, NJ (US); Hong Hu, Edison, NJ (US); Gopinathan K. Menon, Wayne, NJ (US); Kristine Schmalenberg, Warren, NJ (US); John W. Lyga, Basking Ridge, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/164,873

(22) Filed: Jun. 21, 2011

(65) Prior Publication Data

US 2011/0251213 A1 Oct. 13, 2011

Related U.S. Application Data

(60) Division of application No. 12/645,622, filed on Dec. 23, 2009, now Pat. No. 7,993,663, which is a continuation-in-part of application No. 12/344,868, filed on Dec. 29, 2008, now Pat. No. 7,994,175.

(51) Int. Cl.
*A61K 31/497* (2006.01)
*A61K 8/02* (2006.01)
*C07D 401/00* (2006.01)

(52) U.S. Cl. .................... 514/253.12; 424/401; 544/365

(58) Field of Classification Search .................. None
See application file for complete search history.

(56) References Cited

U.S. PATENT DOCUMENTS 6,623,769 B1 9/2003 Lorant et al.
2002/0128270 A1 9/2002 Neya et al.

OTHER PUBLICATIONS

Takeda et al., "Targeted disruption of dermatopontin causes abnormal collagen fibrillogenesis," J. Invest. Dermatol., Sep. 2002;119(3):678-83.

*Primary Examiner* — Yong Chong
*Assistant Examiner* — Jody Karol
(74) *Attorney, Agent, or Firm* — Charles J Zeller; Joan M. McGillycuddy; David M. Joyal

(57) ABSTRACT

Cosmetic compositions comprising 1-aroyl-N-(2-oxo-3-piperidinyl)-2-piperazine carboxamides and methods of using such compositions to impart anti-aging benefits to the skin are disclosed. The 1-aroyl-N-(2-oxo-3-piperidinyl)-2-piperazine carboxamides are believed to have modulatory activity against one or more biochemical pathways implicated in skin aging.

17 Claims, No Drawings

COSMETIC USE OF 1-AROYL-N-(2-OXO-3-PIPERIDINYL)-2-PIPERAZINE CARBOXAMIDES AND RELATED COMPOUNDS

CROSS-REFERENCE TO A RELATED APPLICATION

The present application is a divisional application of parent application U.S. Ser. No. 12/645,622, filed Dec. 23, 2009, now U.S. Pat. No. 7,993,663, which is a continuation-in-part application of parent application U.S. Ser. No. 12/344,868, filed Dec. 29, 2008, now U.S. Pat. No. 7,994,175, which are incorporated herein by reference in its entirety.

FIELD OF INVENTION

The present invention relates generally to compositions for topical application to the skin which comprise 1-aroyl-N-(2-oxo-3-piperidinyl)-2-piperazine carboxamides and the use of such compositions to provide benefits to the skin.

BACKGROUND OF THE INVENTION

The desmogleins are a family of transmembrane proteins which play an important role in cell adhesion, ensuring that cells within tissue are bound together. In skin, they are major components in desmosomes. Desmosomes are cell-cell adhesion complex between epithelial and certain other cell types. They provide mechanical integrity to keratinocytes by linking to keratin intermediate filaments. Desmogleins form the glue that attaches adjacent skin cells, keeping the skin intact. Desmoglein 1 and 3 are both expressed in stratified squamous epithelia. Desmoglein 1 is dominantly expressed in the differentiated upper layer of epidermis, and Desmoglein 3 is mostly found in basal and suprabasal layers. The differential expression pattern of Desmogleins is important for regulating epidermal functions. Changes of Desmoglein 1 and 3 expression pattern in animal models disrupts keratinocyte proliferation and barrier function of skin. An anticipated benefit for the stimulation of Desmogleins would be an increase in anchoring and adhesion between keratinocytes leading to firmer skin and fewer wrinkles.

Collagen is the body's major structural protein and is composed of three protein chains wound together in a tight triple helix. This unique structure gives collagen a greater tensile strength than steel. Approximately 33 percent of the protein in the body is collagen. This protein supports tissues and organs and connects these structures to bones. In fact, bones are also composed of collagen combined with certain minerals such as calcium and phosphorus. Collagen plays a key role in providing the structural scaffolding surrounding cells that helps to support cell shape and differentiation, similar to how steel rods reinforce a concrete block. The mesh-like collagen network binds cells together and provides the supportive framework or environment in which cells develop and function, and tissues and bones heal.

Collagen is created by fibroblasts, which are specialized skin cells located in the dermis. Fibroblasts also produce other skin structural proteins such as elastin (a protein which gives the skin its ability to snap back) and glucosaminoglycans (GAGs). GAGs make up the ground substance that keeps the dermis hydrated. In order to signal or turn on the production of skin structural proteins, fibroblast cells have specially shaped receptors on their outside membranes that act as binding sites to which signal molecules with a matching shape can fit. When the receptors are bound by the correct combination of signal molecules (called fibroblast growth factors, or FGFs), the fibroblast begins the production of collagen. The stimulation of collagen gives the skin its strength, durability, and smooth, plump appearance.

Dermatopontin is a protein component of the extracellular matrix which is located primarily on the surface of the collagen fibers in the skin. Dermatopontin is believed to play important roles in cell-matrix interactions and matrix assembly (collagen fibrillogenesis). Investigation of dermatopontin knockout mice confirm the involvement of dermatopontin in skin elasticity and collagen accumulation, as the elastic modulus of skin was reported to be 57% lower and collagen content was 40% lower in dermatopontin-null mice than in wild-type mice. Takeda et al., "Targeted disruption of dermatopontin causes abnormal collagen fibrillogenesis," *J. Invest. Dermatol,* 2002 September; 119(3):678-83.

It is therefore an object of the invention to provide new compositions and methods for stimulating collagen I, desmogleins, and/or dermatopontin production. It is a further object of the invention to improve the overall appearance of skin, including treating, reversing, and/or preventing signs of aging, such as skin wrinkles, by stimulating collagen I, desmogleins, and/or dermatopontin production with cosmetic compositions comprising effective amounts of 1-aroyl-N-(2-oxo-3-piperidinyl)-2-piperazine carboxamides.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that 1-aroyl-N-(2-oxo-3-piperidinyl)-2-piperazine carboxamides are potent stimulators of collagen I, desmogleins, and/or dermatopontin production and thus are beneficial agents against various signs of intrinsic aging and photo-aging of skin.

In one aspect of the invention, cosmetic compositions are provided for improving the aesthetic appearance of skin comprising, in a cosmetically acceptable vehicle, an effective amount of a collagen I, desmogleins, and/or dermatopontin enhancing 1-aroyl-N-(2-oxo-3-piperidinyl)-2-piperazine carboxamide having the structure of formula 1:

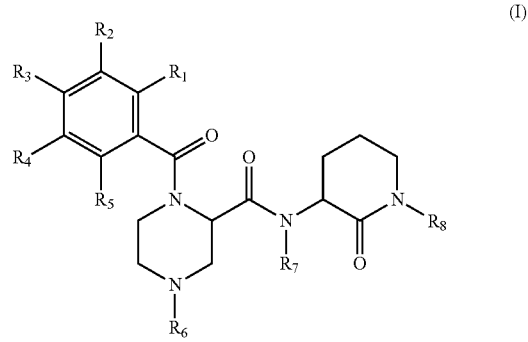

where $R_1$, $R_2$, $R_3$, $R_4$, $R_5$, $R_6$, and $R_7$ are independently hydrogen or a group $—R_9-R_{10}$;

where $R_9$ represents, independently at each occurrence, a bond (i.e., $R_9$ is absent) or one of the following: (i) an aliphatic $C_1$-$C_{20}$ hydrocarbon radical; (ii) a $C_1$-$C_{20}$ aromatic hydrocarbon radical; (iii) a $C_1$-$C_{20}$ heteroaryl radical;

$R_{10}$ is selected independently at each occurrence from hydrogen; —F; —Cl; —Br; —I; —OH, —OR; —$NH_2$; —NHR; —$N(R)_2$; —$N(R)_3^+$; —N(R)—OH; —N(→O)$(R)_2$; —O—$N(R)_2$; —N(R)—O—R; —N(R)—$N(R)_2$; —C=N—R; —N=C$(R)_2$; —C=N—$N(R)_2$; —C(=NR)—$N(R)_2$; —SH; —SR; —CN; —NC; —CHO; —$CO_2H$; —$CO_2^-$; —$CO_2R$; —(C=O)—S—R; —O—(C=O)—H; —O—(C=O)—R; —S—(C=O)—R; —(C=O)—$NH_2$; —(C=O)—$N(R)_2$; —(C=O)—$NHNH_2$; —O—(C=O)—$NHNH_2$; —(C=S)—$NH_2$; —(C=S)—$N(R)_2$; —N(R)—CHO; —N(R)—(C=O)—R; —(C=NR)—O—R; —O—(C=NR)—R, —SCN; —NCS; —NSO; —SSR; —N(R)—C(=O)—$N(R)_2$; —N(R)—C(=S)—$N(R)_2$; —$SO_2$—R; —O—S$(=O)_2$—R; —S$(=O)_2$—OR; —N(R)—$SO_2$—R; —$SO_2$—$N(R)_2$; —O—$SO_3^-$; —O—S$(=O)_2$—OR; —O—S(=O)—OR; —O—S(=O)—R; —S(=O)—OR; —S(=O)—R; —NO; —$NO_2$; —$NO_3$; —O—NO; —O—$NO_2$; —$N_3$; —$N_2$—R; —N($C_2H_4$); —Si(—R)$_3$; —$CF_3$; —O—$CF_3$; —(C=O)—R; —$PR_2$; —O—P(=O)$(OR)_2$; —P(=O)$(OR)_2$; =O; =S; =NR; an aliphatic $C_1$-$C_{20}$ hydrocarbon radical; a $C_1$-$C_{20}$ aromatic hydrocarbon radical; or a $C_1$-$C_{20}$ hacroaryl radical;

where R is independently at each occurrence hydrogen or a saturated, partially saturated, or aromatic $C_1$-$C_{20}$ hydrocarbon radical, including halo and perhalo derivatives thereof;

and where any two adjacent groups $R_1$, $R_2$, $R_3$ $R_4$, and $R_5$ may, together with the phenyl ring to which they are attached, form a five-membered or six-membered aliphatic or aromatic ring, optionally substituted with one or more groups $R_{10}$ and optionally including one or more heteroatoms selected from O, N, S in the ring.

Also provided is a method of treating one or more signs of skin aging comprising topically applying to skin in need thereof a 1-aroyl-N-(2-oxo-3-piperidinyl)-2-piperazine carboxamide according to formula I in an amount effective to enhance collagen I, desmogleins, and/or dermatopontin.

In another aspect of the invention, a method of treating, ameliorating, and/or preventing fine lines or wrinkles or sagging in human skin is provided, comprising topically applying to skin in need thereof, including applying directly to a wrinkle or fine line, a composition comprising a 1-aroyl-N-(2-oxo-3-piperidinyl)-2-piperazine carboxamide according to formula I in an amount effective to enhance collagen I, desmogleins, and/or dermatopontin.

These and other aspects of the present invention will be better understood by reference to the following detailed description and accompanying figures.

DETAILED DESCRIPTION

All terms used herein are intended to have their ordinary meaning unless otherwise provided.

The present invention provides compositions for topical application which comprise and effective amount of 1-aroyl-N-(2-oxo-3-piperidinyl)-2-piperazine carboxamides or a related compound to treat, reverse, ameliorate and/or prevent signs of skin aging. Such signs of skin aging include without limitation, the following:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) decreased by aging and/or menopause;
(n) improvement in skin moisturization; and/or
(o) increase in skin elasticity and/or resiliency;
(p) treatment, reduction, and/or prevention of skin sagging.

In practice, the compositions of the invention are applied to skin in need of treatment. That is, skin which suffers from a deficiency or loss in any of the foregoing attributes or which would otherwise benefit from improvement in any of the foregoing skin attributes.

In certain preferred embodiments the compositions and methods of the invention are directed to the prevention, treatment, and/or amelioration of fine lines and/or wrinkles in the skin. In this case, the compositions are applied to skin in need of treatment, by which is meant skin having wrinkles and/or fine lines. Preferably, the compositions are applied directly to the fine lines and/or wrinkles. The compositions and methods are suitable for treating fine lines and/or wrinkles on any surface of the skin, including without limitation, the skin of the face, neck, and/or hands.

The cosmetic compositions for treating a skin condition associated with loss of collagen and/or elastin fiber comprise, in a cosmetically acceptable vehicle, an amount of a 1-aroyl-N-(2-oxo-3-piperidinyl)-2-piperazinc carboxamides effective to enhance collagen I, desmogleins, and/or dermatopontin. These collagen I, desmogleins, and/or dermatopontin enhancing agents may have the structure of formula (1):

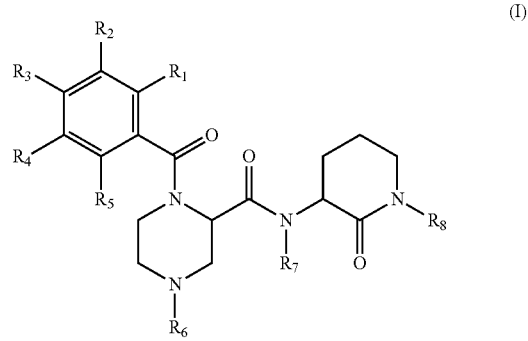

(I)

In formula (I), $R_1$, $R_2$, $R_3$, $R_4$, $R_5$, $R_6$, and $R_7$ are independently hydrogen or a group —$R_9$-$R_{10}$. In one embodiment, at least one of the substituents on the phenyl ring, $R_1$, $R_2$, $R_3$, $R_4$, and $R_5$, will be a group —$R_9$-$R_{10}$ while in other embodiments $R_3$ will be a group —$R_9$-$R_{10}$ and $R_1$, $R_2$, $R_4$, and $R_5$ are hydrogen, such that the phenyl ring is substituted in the para position, or $R_1$ will be a group —$R_9$-$R_{10}$ and $R_2$, $R_2$, $R_4$, and $R_5$ are hydrogen, such that the phenyl ring is substituted in the ortho position, or $R_2$ will be a group —$R_9$-$R_{10}$ and $R_1$, $R_3$, $R_4$, and $R_5$ are hydrogen, such that the phenyl ring is substituted in the meta position.

In one embodiment, $R_7$ and/or $R_8$ represent hydrogen. In other embodiments, $R_7$ and $R_8$ independently represent hydrogen or a group —$R_9$-$R_{10}$, where $R_9$ is typically absent and where $R_{10}$ is preferably a lower alkyl group (e.g., methyl, ethyl, propyl, butyl, etc.), typically methyl. $R_6$ may be hydrogen, but will usually be a group —$R_9$-$R_{10}$. In some embodiments according to formula (I), at least one of $R_6$, $R_7$ and $R_8$ represent a group —$R_9$-$R_{10}$ while in other embodiments $R_6$ a group —$R_9$-$R_{10}$ while $R_7$ and $R_8$ independently represent hydrogen or lower alkyl group (e.g., methyl, ethyl, propyl, butyl, etc.), typically methyl.

In the compounds of formula (I), $R_9$ represents, independently at each occurrence, a bond (i.e., $R_9$ is absent) or one of the following: (i) an aliphatic $C_1$-$C_{20}$ hydrocarbon radical; including an aliphatic $C_1$-$C_{12}$ hydrocarbon radical, an aliphatic $C_1$-$C_8$ hydrocarbon radical, or an aliphatic $C_1$-$C_6$ hydrocarbon radical, as exemplified by substituted or unsubstituted branched, straight chain or cyclic, alkyl, alkenyl (e.g., vinyl, allyl, etc.), and alkynyl moieties; (ii) a $C_6$-$C_{20}$ aromatic hydrocarbon radical, including a $C_6$-$C_{12}$ aromatic hydrocarbon radical, a $C_6$-$C_{10}$ aromatic hydrocarbon radical, or a $C_6$ aromatic hydrocarbon radical, as exemplified by substituted or unsubstituted aryl (e.g., phenyl), alkyl-aryl (e.g., benzyl), aryl-alkyl, and the like; (iii) a $C_1$-$C_{20}$ heteroaryl radical including one or more heteroatoms selected from O, N, and S in the ring; including $C_1$-$C_{12}$ heteroaromatic radicals, $C_1$-$C_8$ heteroaromatic radicals, and $C_1$-$C_6$ heteroaromatic radicals, as exemplified by heteroaryl, alkyl-heteroaryl, heteroaryl-alkyl and the like.

In some embodiments, $R_9$ is absent at one or more occurrences, such that it represents a bond connecting $R_{10}$ directly to the phenyl group or nitrogen atoms of the 1-aroyl-N-(2-oxo-3-piperidinyl)-2-piperazine carboxamide. In other embodiments, $R_9$ represents, independently at each occurrence, a bond (i.e., $R_9$ is absent) or a group selected from linear alkyl moieties of the form —$(CH_2)_a$— where "a" is an integer from 1 to 6, including, for example, —$CH_2$— (methylene), —$CH_2CH_2$—, —$CH_2CH_2CH_2$—, or —$CH_2CH_2CH_2CH_2$—; —$C(CH_3)_2$—, —$CH(CH_3)CH_2$—, —$C(CH_3)_2CH_2$—, —$C_6H_4$—, —$CH_2$—$C_6H_4$—; linear alkoxy moieties of the general form —$(CH_2)_aO$— or —$O(CH_2)_a$— where "a" is an integer from 1 to 6, including for example, —$CH_2O$— or —$OCH_2$—, —$CH_2CH_2O$— or —$OCH_2CH_2$—, —$CH_2CH_2CH_2O$— or —$OCH_2CH_2CH_2$—; —$O(CH_2)_aO$— where "a" is as defined above; or a moiety of the form —$(CH_2)_bO(CH_2)_c$—, —$(CH_2)_bS(CH_2)_c$—, or —$(CH_2)_bNR(CH_2)_c$— wherein "b" and "c" are independently an integer from 0 (zero) to 6 and R is as defined above. In some embodiments, $R_9$ represents a bond, a carbonyl group —(C=O)—, or a methylene group —$CH_2$—.

$R_{10}$ is selected independently at each occurrence from hydrogen; —F; —Cl; —Br; —I; —OH, —OR; —$NH_2$; —NHR; —$N(R)_2$; —$N(R)_3^+$; —N(R)—OH; —N(→O)$(R)_2$; —O—$N(R)_2$; —N(R)—O—R; —N(R)—$N(R)_2$; —C=N—R; —N=$C(R)_2$; —C=N—$N(R)_2$; —C(=NR)—$N(R)_2$; —SH; —SR; —CN; —NC; —CHO; —$CO_2H$; —$CO_2^-$; —$CO_2R$; —(C=O)—S—R; —O—(C=O)—H; —O—(C=O)—R; —S—(C=O)—R; —(C=O)—$NH_2$; —(C=O)—$N(R)_2$; —(C=O)—$NHNH_2$; —O—(C=O)—$NHNH_2$; —(C=S)—$NH_2$; —(C=S)—$N(R)_2$; —N(R)—CHO; —N(R)—(C=O)—R; —(C=NR)—O—R; —O—(C=NR)—R, —SCN; —NCS; —NSO; —SSR; —N(R)—C(=O)—$N(R)_2$; —N(R)—C(=S)—$N(R)_2$; —$SO_2$—R; —O—S(=O)$_2$—R; —S(=O)$_2$—OR; —N(R)—$SO_2$—R; —$SO_2$—$N(R)_2$; —O—$SO_3^-$; —O—S(=O)$_2$—OR; —O—S(=O)—OR; —O—S(=O)—R; —S(=O)—OR; —S(=O)—R; —NO; —$NO_2$; —$NO_3$; —O—NO; —O—$NO_2$; —$N_3$; —N—$R_2$; —$N(C_2H_4)$; —Si$(-R)_3$; —$CF_3$; —O—$CF_3$; —(C=O)—R; —$PR_2$; —O—P(=O)$(OR)_2$; —P(=O)$(OR)_2$; =O; =S; =NR; aliphatic $C_1$-$C_{20}$ hydrocabon radicals; including aliphatic $C_1$-$C_{12}$ hydrocarbon radicals, aliphatic $C_1$-$C_8$ hydrocarbon radicals, or an aliphatic $C_1$-$C_6$ hydrocarbon radicals, as exemplified by substituted or unsubstituted branched, straight chain or cyclic, alkyl, alkenyl (e.g., vinyl, allyl, etc.), and alkynyl moieties; $C_6$-$C_{20}$ aromatic hydrocarbon radicals, including $C_6$-$C_{12}$ aromatic hydrocarbon radicals, $C_6$-$C_{10}$ aromatic hydrocarbon radicals, or $C_6$ aromatic hydrocarbon radicals, as exemplified by substituted or unsubstituted aryl (e.g., phenyl), alkyl-aryl (e.g., benzyl), aryl-alkyl, and the like; or $C_1$-$C_{20}$ heteroaryl radicals including one or more heteroatoms selected from O, N, and S in the ring; including $C_1$-$C_{12}$ heteroaromatic radicals, $C_1$-$C_8$ heteroaromatic radicals, and $C_1$-$C_6$ heteroaromatic radicals, as exemplified by heteroaryl, alkyl-heteroaryl, heteroaryl-alkyl and the like.

R is independently at each occurrence hydrogen or a saturated, partially saturated, or aromatic $C_1$-$C_{20}$ hydrocarbon radical, $C_1$-$C_{12}$ hydrocarbon radical, $C_1$-$C_8$ hydrocarbon radical, or $C_1$-$C_6$ hydrocarbon radical, each optionally including one or more heteroatoms, such as oxygen, sulfur, and nitrogen atoms. Preferably, R is selected from substituted or unsubstituted branched, straight chain or cyclic $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, bicyclic alkyl, aryl, or heteroaryl radicals, and combinations thereof; wherein the foregoing radicals may be substituted with any moiety, including, for example, hydroxyl, amino, cyano, halogen, oxo, carboxy, carboxamide, nitro, azo, alkoxyl, alkyl, alkylimino, alkylamino, dialkylamino, thioalkoxy and combinations thereof. R may be, for example, independently at each occurrence, hydrogen, methyl, ethyl, propyl, butyl, pentyl, hexyl, phenyl, benzyl, or the like, including halo and perhalo derivatives thereof. In some embodiments, R will be hydrogen, methyl, ethyl, phenyl or benzyl, most typically methyl or phenyl.

In formula (I), it will be further understood that any two adjacent groups $R_1$, $R_2$, $R_3$ $R_4$, and $R_5$ may, together with the phenyl ring to which they are attached, form a five-membered or six-membered aliphatic or aromatic ring, optionally substituted with one or more groups $R_{10}$ and optionally including one or more heteroatoms selected from O, N, S in the ring. In some embodiments, any two adjacent groups $R_1$, $R_2$, $R_3$ $R_4$, and $R_5$ may, together with the phenyl ring to which they are attached, form a heterocyclic ring fused to the phenyl ring, which heterocyclic ring may be aromatic, partially saturated, or fully saturated, including, without limitation, four membered rings (azetidine, oxetane, thietane, etc.), five membered rings (pyrrole, pyrrolidine, furan, oxolane, thiophene, thiolane, pyrazole, imidazole, imidazolidine, oxazole, isoxazole, oxazolidine, thiazole, isothiazole, thiazolidine, dioxolane, dithiolane, 1,2,3-triazole, 1,2,4-triazole, dithiazole, tetrazole, etc.), and six membered rings (piperidine, pyridine, tetrahydropyran, pyran, thiane, thiine, piperazine, diazine, oxazine, thiazine, dithiane, dioxane, dioxin, morpholine, quinoline, etc.).

Further, any nitrogen atom may be optionally oxidized to the N-oxide or can be quarternized, for example with lower-alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides such as benzyl and phenethyl bromides, to name a few.

In one embodiment according to formula (I), $R_1$, $R_2$, $R_4$, $R_5$, $R_7$ and $R_8$ represent hydrogen as shown in formula (Ia).

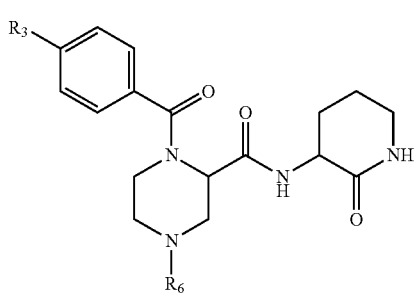

(Ia)

where $R_3$ and $R_6$ are independently hydrogen or a group —$R_9$-$R_{10}$ as defined above. In some embodiments, $R_3$ will be a group —OR (i.e., $R_9$ is absent and $R_{10}$ is —OR), where R represents hydrogen, methyl, ethyl, propyl, iso-propyl, butyl, iso-butyl, sec-butyl, tert-butyl, pentyl, hexyl, phenyl, or benzyl as well as halo and perhalo derivatives thereof, for example trifluoromethyl. In one embodiment, $R_3$ will be a group —OR where R represents methyl to define a methoxy group in the para position of the phenyl ring as shown in formula (Ib):

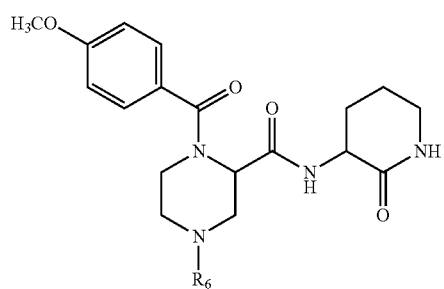

(Ib)

where $R_6$ is hydrogen or a group —$R_9$-$R_{10}$ as defined above. Preferably, $R_6$ is hydrogen or a group —$R_9$-$R_{10}$ where $R_9$ is absent and where $R_{10}$ is selected from (i) acyl groups of the form —(C=O)—R, where R is as defined above, but is typically selected from methyl, ethyl, propyl, butyl, pentyl, hexyl, phenyl, toluyl, or benzyl, (preferably phenyl); and (ii) —$SO_2$—R groups where R is as defined above, but is typically selected from methyl, ethyl, propyl, butyl, pentyl, hexyl, phenyl, toluyl, or benzyl, (preferably methyl). 1-aroyl-N-(2-oxo-3-piperidinyl)-2-piperazine carboxamide compounds according to formula (Ib) where $R_6$ is —(C=O)—$C_6H_5$ (i.e. benzoyl) or —$SO_2$—$CH_3$ are commercially available from Analyticon GmbH (Berlin, Germany).

In a particular embodiment, a cosmetic composition comprises, in a cosmetically acceptable vehicle, preferably a water-in-oil or oil-in-water emulsion, from about 0.0001% to about 90% by weight of a 1-aroyl-N-(2-oxo-3-piperidinyl)-2-piperazine carboxamide having the structure:

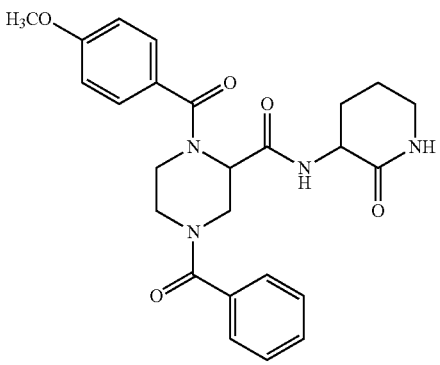

or a cosmetically acceptable salt thereof.

In another particular embodiment, a cosmetic composition comprises, in a cosmetically acceptable vehicle, preferably a water-in-oil or oil-in-water emulsion, from about 0.0001% to about 90% by weight of a 1-aroyl-N-(2-oxo-3-piperidinyl)-2-piperazine carboxamide having the structure:

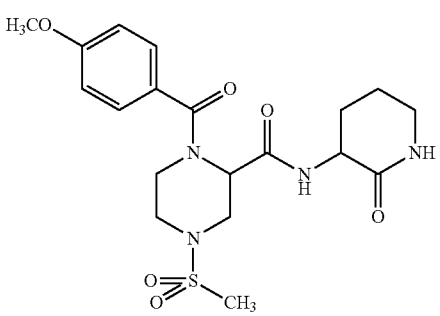

or a cosmetically acceptable salt thereof.

The compounds of formula (1) comprise one stereocenter on the piperazine ring and one sterocenter on the lactam ring. Each of these sterocenters may be in the R or S configuration. Accordingly, the compounds according to formula (i) may exist as a pure (R,R), (R,S), (S,R), or (S,S) diastereomer with respect to these two chiral centers or may comprise a mixture of two or more diastereomer. By "pure" is meant that the particular diastereomer comprises at least 95% by weight of the total weight of formula (I) compound, and preferably at least 98% or at least 99% by weight.

The invention embraces the use of cosmetically or pharmaceutically acceptable (e.g., non-toxic and/or non-irritating) salts. Examples of the salts of the compounds in the present invention include salts with alkali metals such as sodium and potassium; salts with alkaline-earth metals such as calcium and magnesium; salts with amines such as monoethanolamine; salts with inorganic acids such as hydrochloric acid and sulfuric acid; and salts with organic acids such as citric acid and acetic acid. Special mention may be made of hydrochloride salts.

The cosmetic compositions according to the invention can be formulated in a variety of forms for topical application and will comprise from about 0.0001% to about 90% by weight of one or more compounds according to formula (I), and preferably will comprise from about 0.001% to about 25% by weight, and more preferably from about 0.01% to about 10% by weight. The compositions will comprise and effective amount of the 1-aroyl-N-(2-oxo-3-piperidinyl)-2-piperazine carboxamide compounds according to formula (I), by which is meant an amount sufficient to enhance collagen I, desmogleins, and/or dermatopontin in given area of skin when topically applied thereto.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The compositions can include a cosmetically acceptable vehicle. Such vehicles may take the form of any known in the art suitable for application to skin and may include water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion preferably has one or more organic compounds, including emollients; humectants (such as propylene glycol and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as C12 isoparaffin (isododecane) manufactured by the Permethyl Corporation having the tradename Permethyl 99ATM are also contemplated to be suitable. Various commercially available $C_{16}$ isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystaline wax, silicone waxes, fluorinated waxes, and any combination thereof.

Non-limiting emulsifiers included emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, fatty acids such as stearic acid, fatty acid salts, and mixtures thereof. The preferred emulsifiers include soya sterol, cetyl alcohol, stearic acid, emulsifying wax, and mixtures thereof. Other specific emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, below 1% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)m- and/or -(PO)n-groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

The compositions may include liposomes. The liposomes may comprise other additives or substances and/or may be modified to more specifically reach or remain at a site following administration.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives, stabilizers, pharmaceutical agents, photostabilizing agents, sunscreens, and mixtures thereof. In addition to the foregoing, the cosmetic compositions of the invention may contain any other compound for the treatment of skin disorders.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions may include additional skin actives such as, but are not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Amorphophallus campanulatus, Anogeissus latifolia, Asmunda japonica, Azadirachta indica, Butea frondosa, Butea monosperma, Cedrus deodara, Derris scandens* Benth., *Emblica officinalis, Ficus benghalensis, Glycyrrhiza glabra, Harungana madagascariensis, Humulus scandens, Ilex purpurea Hassk, Innula racemosa, Ligusticum chiangxiong, Ligusticum lucidum, Mallotus philippinensis, Melicope hayesii, Mimusops elengi, Morinda citrifolia, Moringa oleifera, Naringi crenulata, Nerium indicum, Portulaca oleracea, Portulaca sativa, Psoralea corylifolia, Sapindus rarak, Sesbania grandaflora, Stenoloma chusana, Tiliacora triandra, Terminalia bellerica*, tomato glycolipid, and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethyl-methacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

It is preferred that the composition be essentially free of components having a strong oxidizing potential, including for example, organic or inorganic peroxides. By "essentially free of" these components is meant that the amounts present are insufficient to have a measurable impact on the collagen I, desmogleins, and/or dermatopontin enhancing activity of the 1-aroyl-N-(2-oxo-3-piperidinyl)-2-piperazine carboxamides. In some embodiments, this will be, on a molar basis in relation to the amount of 1-aroyl-N-(2-oxo-3-piperidinyl)-2-piperazine carboxamide, less than 1%.

In one embodiment, the composition of the invention comprising a 1-aroyl-N-(2-oxo-3-piperidinyl)-2-piperazine carboxamide may have a pH between about 1 and about 8. In certain embodiments, the pH of the composition will be acidic, i.e., less than 7.0., and preferably will be between about 2 and about 7, more preferably between about 3.5 and about 5.5.

The invention provides a method for treating aging skin by topically applying a composition comprising a 1-aroyl-N-(2-oxo-3-piperidinyl)-2-piperazine carboxamide, preferably in a cosmetically acceptable vehicle, over the affected area for a period of time sufficient to reduce, ameliorate, reverse or prevent dermatological signs of aging. This method is particularly useful for treating signs of skin photoaging and intrinsic aging.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance,and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

Without wishing to be bound by any particular theory, it is believed that the compositions of the present invention enhance and improve the aesthetic appearance of skin by stimulation of collagen and/or by improving the cell-to-cell adhesion between keratinocytes through the stimulation of Desmogleins.

The composition will typically be applied to the skin one, two, or three times daily for as long as is necessary to achieve desired anti-aging results. The treatment regiment may comprise daily application for at least one week, at least two weeks, at least four weeks, at least eight weeks, or at least twelve weeks. Chronic treatment regimens are also contemplated.

The 1-aroyl-N-(2-oxo-3-piperidinyl)-2-piperazine carboxamide active component is topically applied to an "individual in need thereof," by which is meant an individual that stands to benefits from reducing visible signs of skin damage or aging. In a specific embodiment, the 1-aroyl-N-(2-oxo-3-piperidinyl)-2-piperazine carboxamide component is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive 1-aroyl-N-(2-oxo-3-piperidinyl)-2-piperazine carboxamide compositions to the skin of an individual in need thereof, e.g., topically application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles on the skin of the hands, arms, legs, neck, chest, and face, including the forehead, It is also contemplated that the compositions of the invention will be useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in patients that have not manifested signs of skin aging, most commonly in individuals under 25 years of age. The method may also reverse or treat signs of aging once manifested as is common in patients over 25 years of age.

EXAMPLES

1. Example 1

Stimulation of Collagen 1

Human dermal fibroblasts (Cascade Biologics) were cultured in 96-well tissue culture plates in growth medium (DMEM, 5% FBS, 1% L-Glut, and 1% antibiotics) and incubated for 24 hours at 37° C. Cells were then treated with test active diluted in growth medium and incubated for 48 hours at 37° C., after which the culture media was collected and assayed for the presence of procollagen 1. Procollagen 1 levels were assayed using an ELISA kit from Takara (Procollagen Type-1 C-Peptide EIA Kit, Takara Bio Inc.) as per manufacturer's instructions. Fibroblasts treated with 5 µg/ml of 1-aroyl-N-(2-oxo-3-piperidinyl)-2-piperazine carboxamide showed a 75.4% increase in collagen synthesis compared to control.

2. Example 2

Stimulation of Desmogleins

Normal human keratinocytes were cultured in 96 well tissue culture treated plates in Epilife medium with growth supplements (Cascade Biologics Inc.). Cells were treated with test material or a dimethylsulfoxide vehicle control diluted in growth medium for 24 hours in a humidified 37° C. incubator with 10% CO2. After incubation, growth medium from each plate was removed and 100 µl of lysis buffer was added to each of the wells and placed in the humidified 37° C. incubator with 10% $CO_2$ for 30 minutes. At the end of the incubation period, the cells were collected in freezer plates and placed in a −80° C. freezer, until analysis. Changes in mRNA for Desmoglein 3 (DSG3) after treatment were analysed using Panomics Quantigene multiplex assay that employs branched DNA technology. The increase (%) in mRNA for each endpoint was calculated by comparing the test results of the extract to the control.

Keratinocytes treated with 1-aroyl-N-(2-oxo-3-piperidinyl)-2-piperazine carboxamide at a concentration of 0.0005% showed a 95% increase in Desmoglein 1 expression after 24 hours. The effect observed was an average of three samples assayed and was statistically significant at $p<0.05$. Treatment with 0.00005% of the test material did not show a statistically significant increase in Desmoglein 1 expression.

3. Example 3

Stimulation of Dermatopontin Production

Normal human dermal fibroblasts were cultured in 96 well tissue culture treated plates, containing appropriate culture medium. Cells were treated with 1-aroyl-N-(2-oxo-3-piperidinyl)-2-piperazine carboxamide test material, diluted in growth medium, for 24 hours in a humidified 37° C. incubator with 10% $CO_2$. After incubation, growth medium from each plate was removed and 100 μl of lysis buffer was added to the wells and placed in 37° C. incubator with 10% $CO_2$ for 30 minutes. At the end of incubation, the cells were collected in freezer plates and placed in −80° C. freezer, until analysis. Changes in mRNA for Dermatopontin after treatment were analysed using Panomics Quantigene multiplex assay that employs a branched DNA technology. Percent increase in mRNA for MT2A was calculated by comparing the test results to that of the vehicle control. Fibroblasts treated with 0.0005% or 0.00005% of 1-aroyl-N-(2-oxo-3-piperidinyl)-2-piperazine carboxamide showed a 62% and 43% stimulation in mRNA levels for Dermatopontin respectively. All results reported are statistically significant at $p<0.05$.

4. Example 4

Representative Formulations

Representative formulations of skin care products comprising effective amounts of 1-aroyl-N-(2-oxo-3-piperidinyl)-2-piperazine carboxamide active agent are provided in Table 1.

TABLE 1

| | | Concentration (wt. %) | | | |
|---|---|---|---|---|---|
| Description | Purpose | Formula 1 | Formula 2 | Formula 3 | Formula 4 |
| Deionized water | diluent | qs 100% | qs 100% | qs 100% | qs 100% |
| Acrylates/C10-30 Alkyl Acrylate Crosspolymer | emulsifier | 1 | 1 | 1 | 1 |
| Cetyl Ethylhexanoate | emollient | 10 | 10 | 10 | 10 |
| C12-15 Alkyl Benzoate | emollient | 3.9 | 3.9 | 3.9 | 3.9 |
| Isopropyl Isostearate | emollient | 3 | 3 | 3 | 3 |
| Diisopropyl dimer dillinoleate | emollient | 0.1 | 0.1 | 0.1 | 0.1 |
| Tocopheryl acetate | anti-oxidant | 0.5 | 0.5 | 0.5 | 0.5 |

TABLE 1-continued

| | | Concentration (wt. %) | | | |
|---|---|---|---|---|---|
| Description | Purpose | Formula 1 | Formula 2 | Formula 3 | Formula 4 |
| Butylene glycol | humectant | 2 | 2 | 2 | 2 |
| Propylene glycol | humectant | 1 | 1 | 1 | 1 |
| Dimethicone PEG-7 isostearate | co-emulsifier | 0.5 | 0.5 | 0.5 | 0.5 |
| Methyl gluceth-20 | humectant | 0.5 | 0.5 | 0.5 | 0.5 |
| Triethanolamine | neutralizer | 1 | 1 | 1 | 1 |
| Acrylates/acrylamide copolymer/mineral oil | emulsifier | 1.5 | 1.5 | 1.5 | 1.5 |
| DMDM Hydantoin/Iodopropynyl-butylcarbonate | preservative | 0.4 | 0.4 | 0.4 | 0.4 |
| 1-aroyl-N-(2-oxo-3-piperidinyl)-2-piperazine carboxamide | active | 0.3 | 0.03 | 0.01 | 0.005 |

Formulas 1-4 are topically applied to skin, including skin of the face, to prevent, treat, and/or reduce signs of photoaging and/or intrinsic aging, such as fine lines and wrinkles. The formulas are topically applied to the skin for an amount of time sufficient to provide a clinically measurable reduction in one or more signs of skin aging, which typically entails once, twice, or three-times daily treatment for one, two, or three weeks up to about eight weeks or more, including chronic treatment.

5. Example 5

Synthesis of Representative Compound

The synthesis of a representative 1-aroyl-N-(2-oxo-3-piperidinyl)-2-piperazine carboxamide from pyrazine 2-carboxylic acid following is shown in the scheme below.

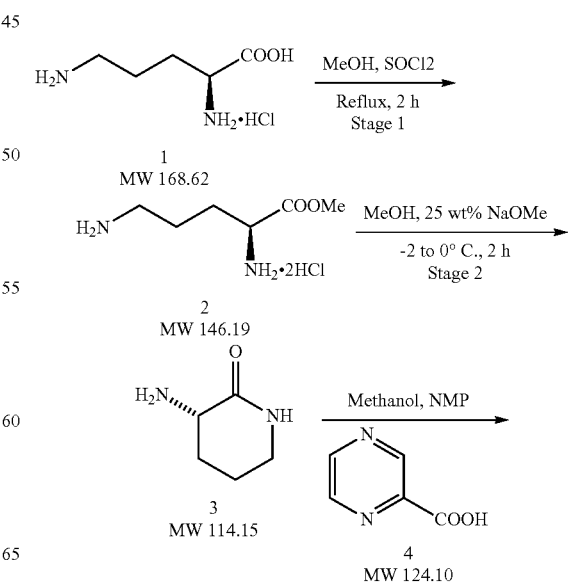

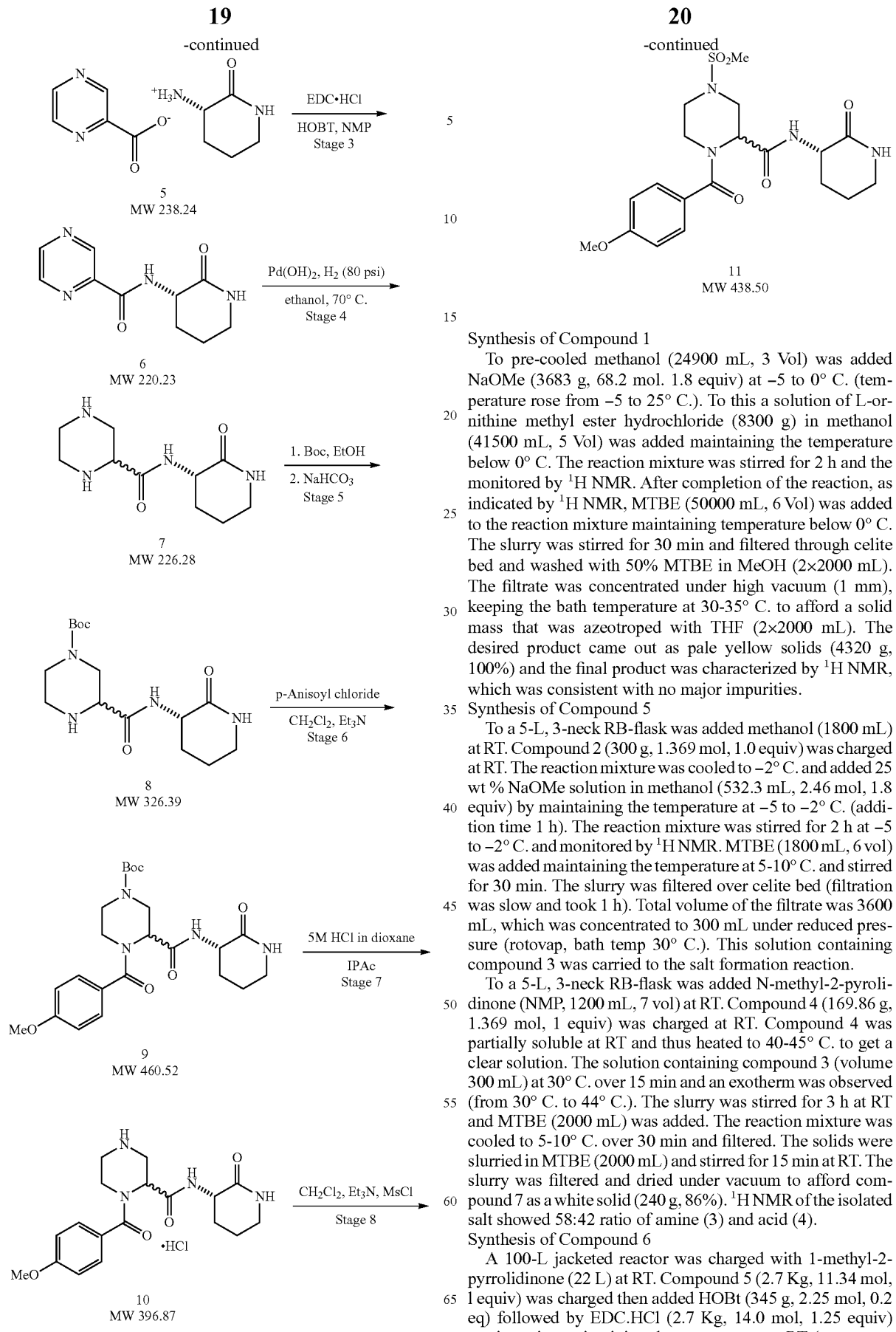

Synthesis of Compound 1

To pre-cooled methanol (24900 mL, 3 Vol) was added NaOMe (3683 g, 68.2 mol. 1.8 equiv) at −5 to 0° C. (temperature rose from −5 to 25° C.). To this a solution of L-ornithine methyl ester hydrochloride (8300 g) in methanol (41500 mL, 5 Vol) was added maintaining the temperature below 0° C. The reaction mixture was stirred for 2 h and the monitored by $^1$H NMR. After completion of the reaction, as indicated by $^1$H NMR, MTBE (50000 mL, 6 Vol) was added to the reaction mixture maintaining temperature below 0° C. The slurry was stirred for 30 min and filtered through celite bed and washed with 50% MTBE in MeOH (2×2000 mL). The filtrate was concentrated under high vacuum (1 mm), keeping the bath temperature at 30-35° C. to afford a solid mass that was azeotroped with THF (2×2000 mL). The desired product came out as pale yellow solids (4320 g, 100%) and the final product was characterized by $^1$H NMR, which was consistent with no major impurities.

Synthesis of Compound 5

To a 5-L, 3-neck RB-flask was added methanol (1800 mL) at RT. Compound 2 (300 g, 1.369 mol, 1.0 equiv) was charged at RT. The reaction mixture was cooled to −2° C. and added 25 wt % NaOMe solution in methanol (532.3 mL, 2.46 mol, 1.8 equiv) by maintaining the temperature at −5 to −2° C. (addition time 1 h). The reaction mixture was stirred for 2 h at −5 to −2° C. and monitored by $^1$H NMR. MTBE (1800 mL, 6 vol) was added maintaining the temperature at 5-10° C. and stirred for 30 min. The slurry was filtered over celite bed (filtration was slow and took 1 h). Total volume of the filtrate was 3600 mL, which was concentrated to 300 mL under reduced pressure (rotovap, bath temp 30° C.). This solution containing compound 3 was carried to the salt formation reaction.

To a 5-L, 3-neck RB-flask was added N-methyl-2-pyrolidinone (NMP, 1200 mL, 7 vol) at RT. Compound 4 (169.86 g, 1.369 mol, 1 equiv) was charged at RT. Compound 4 was partially soluble at RT and thus heated to 40-45° C. to get a clear solution. The solution containing compound 3 (volume 300 mL) at 30° C. over 15 min and an exotherm was observed (from 30° C. to 44° C.). The slurry was stirred for 3 h at RT and MTBE (2000 mL) was added. The reaction mixture was cooled to 5-10° C. over 30 min and filtered. The solids were slurried in MTBE (2000 mL) and stirred for 15 min at RT. The slurry was filtered and dried under vacuum to afford compound 7 as a white solid (240 g, 86%). $^1$H NMR of the isolated salt showed 58:42 ratio of amine (3) and acid (4).

Synthesis of Compound 6

A 100-L jacketed reactor was charged with 1-methyl-2-pyrrolidinone (22 L) at RT. Compound 5 (2.7 Kg, 11.34 mol, 1 equiv) was charged then added HOBt (345 g, 2.25 mol, 0.2 eq) followed by EDC.HCl (2.7 Kg, 14.0 mol, 1.25 equiv) portion wise maintaining the temperature at RT (some exotherm was observed, temperature rose from 25° C. to 30° C.). The reaction mixture was stirred at RT for 24 h and monitored by HPLC and ELSD. No starting materials were observed. MeOH (5.4 L) followed by MTBE (21 L) were added at RT and stirred for 30 min maintaining the temperature at 5-10° C. The solids were filtered and washed with MTBE (12 L). The product was dried in vacuum oven.

Synthesis of Compound 7

N-(2-Oxopiperidin-3-yl) pyrazine-2-carboxamide (6) (2.6 Kg, 99% pure by HPLC) and Pd(OH)$_2$ (520 g) were charged to a 50-L reactor and ethanol (39 L, 15 vol) was added. The mixture was purged with nitrogen twice and allowed to stir at 70° C. under hydrogen atmosphere (80 psi) for 12 h. TLC (50:50 MeOH/Ethyl acetate) analysis showed formation of product (no starting material). The reaction mixture was cooled to RT and filtered through a celite bed. The celite bed was washed with of EtOH/CH$_2$Cl$_2$ (50:50) (2×19.5 L). Solvent was evaporated under reduced pressure. Product was obtained as a thick liquid. To this was added methylene chloride (10 vol) and swapped the residual ethanol under reduced pressure at 45° C. Methylene chloride (2×5 vol) was added and swapped the residual solvent under reduced pressure at 45° C. The product was obtained as off-white solids (2.85 kg). $^1$H NMR was consistent and showed 4% ethanol and 94% pure by ELSD. The product can then be dried.

Synthesis of Compound 8

Synthesis of compound 8 was performed on 350.0 g (7) scale.

TABLE 2

| Entry | Scale (7) | Conditions | Yield | Comments |
|---|---|---|---|---|
| 1 | 350 g | 7 (1.548 mol), Boc anhydride (0.9 equiv), MeOH: CH$_2$Cl$_2$ [1:19, total 20 vol], | 260 g (51.5%)[1] | Confirmed by $^1$H NMR and ELSD. |

[1] not isolated; yield was determined from LOD of an aliquot

To a solution of compound 7 (350 g, 1.0 equiv) in methanol (1.0 vol) and methylene chloride (14 vol) was added a solution of (Boc)$_2$O (0.9 equiv) in CH$_2$Cl$_2$ (5 vol) drop wise over 6 h at 0-5° C. The reaction progress was monitored by TLC and ELSD. After completion of the addition no starting material was observed. To the reaction mixture was added brine solution (400 mL, 5 vol) and stirred for 15 minutes then separated the aqueous layer and extracted with methylene chloride (3×500 mL). 15% Citric acid solution (7 vol) was added and stirred for 15 minutes. The aqueous layer was separated and basified with 3 N NaOH solution (5 vol) then extracted with methylene chloride (30 vol). The organic phase was washed with brine (750 mL), concentrated approximately to 10 vol and the solution (KF 0.1%) was taken into the next step. The yield of 8 was determined to be 51.5% based on LOD analysis of little aliquot. Mono Boc protection can also be optimized in water.

Synthesis of Compound 9

TABLE 3

| Entry | Scale (8) | Conditions | Yield | Comments |
|---|---|---|---|---|
| 1 | 260 g[1] | 8 (1.0 equiv, solution from previous step), 4-methoxybenzol chloride | 366 g (assumed to be quantitative) | HPLC purity: 91% (AUC) by HPLC |

TABLE 3-continued

| Entry | Scale (8) | Conditions | Yield | Comments |
|---|---|---|---|---|
| | | (1.0 equiv), Et$_3$N(2.0 equiv), CH$_2$Cl$_2$(10 vol) | | |

[1] not isolated; taken solution from previous step into this step; yield was determined from LOD of an aliquot.

To a solution of compound 8 in methylene chloride was added Et$_3$N (2.0 equiv) and the mixture was stirred at 0-5° C. for 10 minutes then added 4-methoxybenzoyl chloride (p-anisoyl chloride) drop-wise over 30 min. The reaction progress was monitored by TLC and after 1 h no starting material was observed. To the reaction mixture was added 15% citric acid solution (5 vol) and separated organic layer washed with 1 N NaOH solution (5 vol). The organic phase was washed with brine and concentrated to approximately 2 vol and then added 5 vol of IPAc. The solution was concentrated again to approximately 2 vol (a sample was submitted for OVI analysis). Finally the clear solution (submitted for KF analysis) was diluted with 3 vols of IPAc (total 5 vol, 1.75 L) and taken into the next step. The yield of the solution was assumed to be quantitative.

Synthesis of Compound 10

TABLE 4

| Entry | Scale (9) | Conditions | Yield | Comments |
|---|---|---|---|---|
| 1 | 366 g[1] | 9 (1.0 equiv, solution in IPAc from previous step), 5 M HCl in dioxane (2.5 equiv) | 510 g[2] (~90%, 93% (AUC) by HPLC) | Isolated as HCl salt (can be handled isolation under nitrogen) |

[1] Crude yield from previous step was determined from LOD of solution from Boc protection step.
[2] Contains 40% of IPAc; drying is in progess. The purity may be upgraded using hot EtOAc slurry.

To a solution of compound 9 from the previous step was added 5 M HCl in dioxane (2.5 equiv) slowly at 10° C. and the slurry stirred at room temperature for 14 h. The reaction progress was monitored by TLC and HPLC, and it showed 11% starting material by HPLC (the reaction mixture was a slurry and analysis may not be accurate). The mixture was diluted with 2 vol of IPAc and stirred for 1 h. The solids were filtered, washed with IPAc. Wet wt: 515 g (contains 40% IPAc by NMR analysis). Yield: 50% over 3 steps (Boc protection, benzoylation and deprotection).

Synthesis of 11 (a 1-aroyl-N-(2-oxo-3-piperidinyl)-2-piperazine carboxamide)

Synthesis of a representative 1-aroyl-N-(2-oxo-3-piperidinyl)-2-piperazine carboxamide was performed on 45.0 g scale

TABLE 5

| Entry | Scale | Conditions | Yield | Comments |
|---|---|---|---|---|
| 1 | 45.0 g | 10, MsCl (1.1 equiv), Et$_3$N (2.0 equiv), CH$_2$Cl$_2$ (10 vol), rt | 40.0 g (73%) | Confirmed by $^1$H NMR and HPLC (95%) |

To a solution of compound 10 (45.0 g freebase, 0.125 mol, 1.0 equiv) in dichloromethane (10 vol) was added triethylamine (25.4 g, 0.25 mol, 2.0 equiv) and stirred the reaction mixture at 0-5° C. for 10 minutes, then mesylchloride (1.1 equiv) added drop wise. After completion of the addition, the reaction mixture was stirred for 1 h (reaction progress was monitored by TLC and HPLC). The reaction was deemed to be completed when <2% starting material remained. The reaction mixture was quenched with saturated bicarbonate solution (225 mL, 5 vol) and diluted with 200 mL of dichloromethane. The organic phase was separated, washed with 1 N HCl, dried and concentrated to give compound 11 (a 1-aroyl-N-(2-oxo-3-piperidinyl)-2-piperazine carboxamide) (40.0 g, 73%) as an off-white solid. NMR was consistent and 95.5% purity was determined by HPLC. An HCl salt of compound 10 may be used in a scale up reaction.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for providing a benefit to human skin comprising topically applying to the skin of an individual in need thereof an effective amount of a 1-aroyl-N-(2-oxo-3-piperidinyl)-2-piperazine carboxamide compound or a diastereomer or cosmetically acceptable salt thereof in a cosmetically acceptable vehicle, wherein said 1-aroyl-N-(2-oxo-3-piperidinyl)-2-piperazine carboxamide compound, or diastereomer or cosmetically acceptable salt thereof, has the structure of formula (Ia):

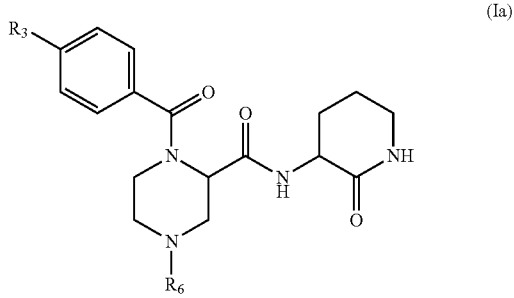

(Ia)

where $R_3$ and $R_6$ are independently hydrogen or a group —$R_9$-$R_{10}$;

$R_9$ represents, independently at each occurrence, a bond; an aliphatic $C_1$-$C_{20}$ hydrocarbon radical; a $C_1$-$C_{20}$ aromatic hydrocarbon radical; or a $C_1$-$C_{20}$ heteroaryl radical;

$R_{10}$ is selected independently at each occurrence from hydrogen; —F; —Cl; —Br; —I; —OH; —OR; —NH$_2$; —NHR; —N(R)$_2$; —N(R)$_3^+$; —N(R)—OH; —N(→O)(R)$_2$; —O—N(R)$_2$; —N(R)—O—R; —N(R)—N(R)$_2$; —C=N—R; —N=C(R)$_2$; —C=N—N(R)$_2$; —C(=NR)—N(R)$_2$; —SH; —SR; —CN; —NC; —CHO; —CO$_2$H; —CO$_2^-$; —CO$_2$R; —(C=O)—S—R; —O—(C=O)—H; —O—(C=O)—R; —S—(C=O)—R; —(C=O)—NH$_2$; —(C=O)—N(R)$_2$; —(C=O)—NHNH$_2$; —O—(C=O)—NHNH$_2$; —(C=S)—NH$_2$; —(C=S)—N(R)$_2$; —N(R)—CHO; —N(R)—(C=O)—R; —(C=NR)—O—R; —O—(C=NR)—R; —SCN; —NCS; —NSO; —SSR; —N(R)—C(=O)—N(R)$_2$; —N(R)—C(=S)—N(R)$_2$; —SO$_2$—R; —O—S(=O)$_2$—R; —S(=O)$_2$—OR; —N(R)—SO$_2$—R; —SO$_2$—N(R)$_2$; —O—SO$_3^-$; —O—S(=O)$_2$—OR; —O—S(=O)—OR; —O—S(=O)—R; —S(=O)—OR; —S(=O)—R; —NO; —NO$_2$; —NO$_3$; —O—NO; —O—NO$_2$; —N$_3$; —N$_2$; —N(C$_2$H$_4$); —Si(—R)$_3$; —CF$_3$; —O—CF$_3$; —(C=O)—R; —PR$_2$; —O—P(=O)(OR)$_2$; —P(=O)(OR)$_2$; =O; =S; =NR; an aliphatic $C_1$-$C_{20}$ hydrocarbon radical; a $C_1$-$C_{20}$ aromatic hydrocarbon radical; or a $C_1$-$C_{20}$ heteroaryl radical;

where R is independently at each occurrence hydrogen or a saturated, partially saturated, or aromatic $C_1$-$C_{20}$ hydrocarbon radical or halogenated derivative thereof.

2. The method according to claim 1, where $R_3$ represents a group —OR.

3. The method according to claim 2, where $R_3$ represents —OCH$_3$.

4. The method according to claim 1, where $R_6$ is a group —(C=O)—R, where R is selected from the group consisting of methyl, ethyl, propyl, butyl, pentyl, hexyl, phenyl, toluyl, or benzyl.

5. The method according to claim 4, where $R_6$ is a group —(C=O)—(C$_6$H$_5$).

6. The method according to claim 1, where $R_6$ is a group —SO$_2$—R, where R is selected from the group consisting of methyl, ethyl, propyl, butyl, pentyl, hexyl, phenyl, toluyl, or benzyl.

7. The method according to claim 6, where $R_6$ is a group —SO$_2$—CH$_3$.

8. The method according to claim 1, wherein said skin benefit is selected from the group consisting of:

(a) treatment and/or reduction of fine lines or wrinkles, and/or reduction of severity of existing fine lines or wrinkles and/or inhibition of formation of new fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by menopause;
(n) improvement in skin moisturization;
(o) increase in skin elasticity and/or resiliency; or
(p) treatment and/or reduction of skin sagging.

9. The method according to claim 8, wherein said skin benefit is the treatment and/or reduction of fine lines or wrinkles and/or reduction of severity of existing fine lines or wrinkles and/or inhibition of formation of new fine lines or wrinkles.

10. The method according to claim 8, wherein said skin benefit is the treatment and/or reduction of skin sagging.

11. The method according to claim 1, wherein said 1-aroyl-N-(2-oxo-3-piperidinyl)-2-piperazine carboxamide compound has the structure:

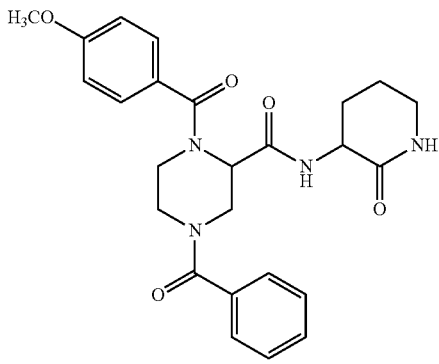

or a diastereomer or a cosmetically acceptable salt thereof.

12. The method according to claim 1, wherein said 1-aroyl-N-(2-oxo-3-piperidinyl)-2-piperazine carboxamide compound has the structure:

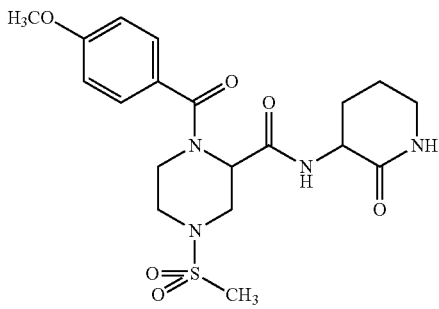

or a diastereomer or a cosmetically acceptable salt thereof.

13. A method for treating wrinkles and/or fine lines comprising topically applying to said wrinkle and/or fine line on the skin of an individual in need thereof an effective amount of a 1-aroyl-N-(2-oxo-3-piperidinyl)-2-piperazine carboxamide compound or a diastereomer or a cosmetically acceptable salt thereof in a cosmetically acceptable vehicle for a time sufficient to reduce the severity of said wrinkles or fine lines.

14. The method according to claim 1, wherein a (R,R) diastereomer comprises at least 95% by weight of the total weight of said compound having the structure of formula (Ia).

15. The method according to claim 1, wherein a (R,S) diastereomer comprises at least 95% by weight of the total weight of said compound having the structure of formula (Ia).

16. The method according to claim 1, wherein a (S,R) diastereomer comprises at least 95% by weight of the total weight of said compound having the structure of formula (Ia).

17. The method according to claim 1, wherein a (S,S) diastereomer comprises at least 95% by weight of the total weight of said compound having the structure of formula (Ia).

* * * * *